(12) United States Patent
Schneider

(10) Patent No.: US 10,577,268 B2
(45) Date of Patent: Mar. 3, 2020

(54) METHOD FOR TREATING DANGEROUS LIQUIDS FOR DUMPING

(71) Applicant: Heribert Schneider, Granada (ES)

(72) Inventor: Heribert Schneider, Granada (ES)

( * ) Notice: Subject to any disclaimer, the term of this patent is extended or adjusted under 35 U.S.C. 154(b) by 58 days.

(21) Appl. No.: 16/063,292

(22) PCT Filed: Dec. 2, 2016

(86) PCT No.: PCT/ES2016/070857
§ 371 (c)(1),
(2) Date: Jun. 18, 2018

(87) PCT Pub. No.: WO2017/103304
PCT Pub. Date: Jun. 22, 2017

(65) Prior Publication Data
US 2018/0370832 A1    Dec. 27, 2018

(30) Foreign Application Priority Data
Dec. 17, 2015   (ES) .................................. 201500923

(51) Int. Cl.
*C02F 9/00*       (2006.01)
*C02F 1/04*       (2006.01)
*C02F 1/00*       (2006.01)
*C02F 1/66*       (2006.01)
*C02F 1/28*       (2006.01)
*C02F 1/32*       (2006.01)
*C02F 1/50*       (2006.01)
*C02F 103/00*     (2006.01)

(52) U.S. Cl.
CPC ............. *C02F 9/00* (2013.01); *C02F 1/008* (2013.01); *C02F 1/04* (2013.01); *C02F 1/283* (2013.01); *C02F 1/32* (2013.01); *C02F 1/50* (2013.01); *C02F 1/66* (2013.01); *C02F 2103/003* (2013.01); *C02F 2209/006* (2013.01); *C02F 2209/05* (2013.01); *C02F 2209/06* (2013.01); *C02F 2303/04* (2013.01)

(58) Field of Classification Search
CPC .... C02F 9/00; C02F 1/008; C02F 1/04; C02F 1/283; C02F 1/32; C02F 1/50; C02F 1/66; C02F 2103/003; C02F 2209/006; C02F 2209/05; C02F 2209/06; C02F 2303/04
USPC ........................................................ 588/318
See application file for complete search history.

(56) References Cited

U.S. PATENT DOCUMENTS 4,940,134 A * 7/1990 Aoki ..................... B01D 1/0017
159/11.1

* cited by examiner

*Primary Examiner* — Edward M Johnson

(57) ABSTRACT

The invention relates to a method for treating dangerous liquids for dumping in situ in a plant having an electrical panel (1) with an automaton processor, comprising the following steps: collecting in accumulation tanks (2); evaporating, in an automatic filling evaporator (6), via internal or external heating; condensing in a condenser (7), in direct or indirect contact with the vapour of the evaporator (6), converting said vapour into distillate; neutralising via reagents, in a neutralisation reactor (8), to a pH controlled by a pH and conductivity probe (14), with pH+ and pH+ reagents; filtering the waste via an active carbon filter (9) and dosing disinfectant therein, before expulsion via the drainage outlet of the sewer (32); safety disinfecting with ultraviolet light (17); and taking samples of the waste, by means of the sample-taking tap (16) provided before the outlet of the sewer (32).

7 Claims, 1 Drawing Sheet

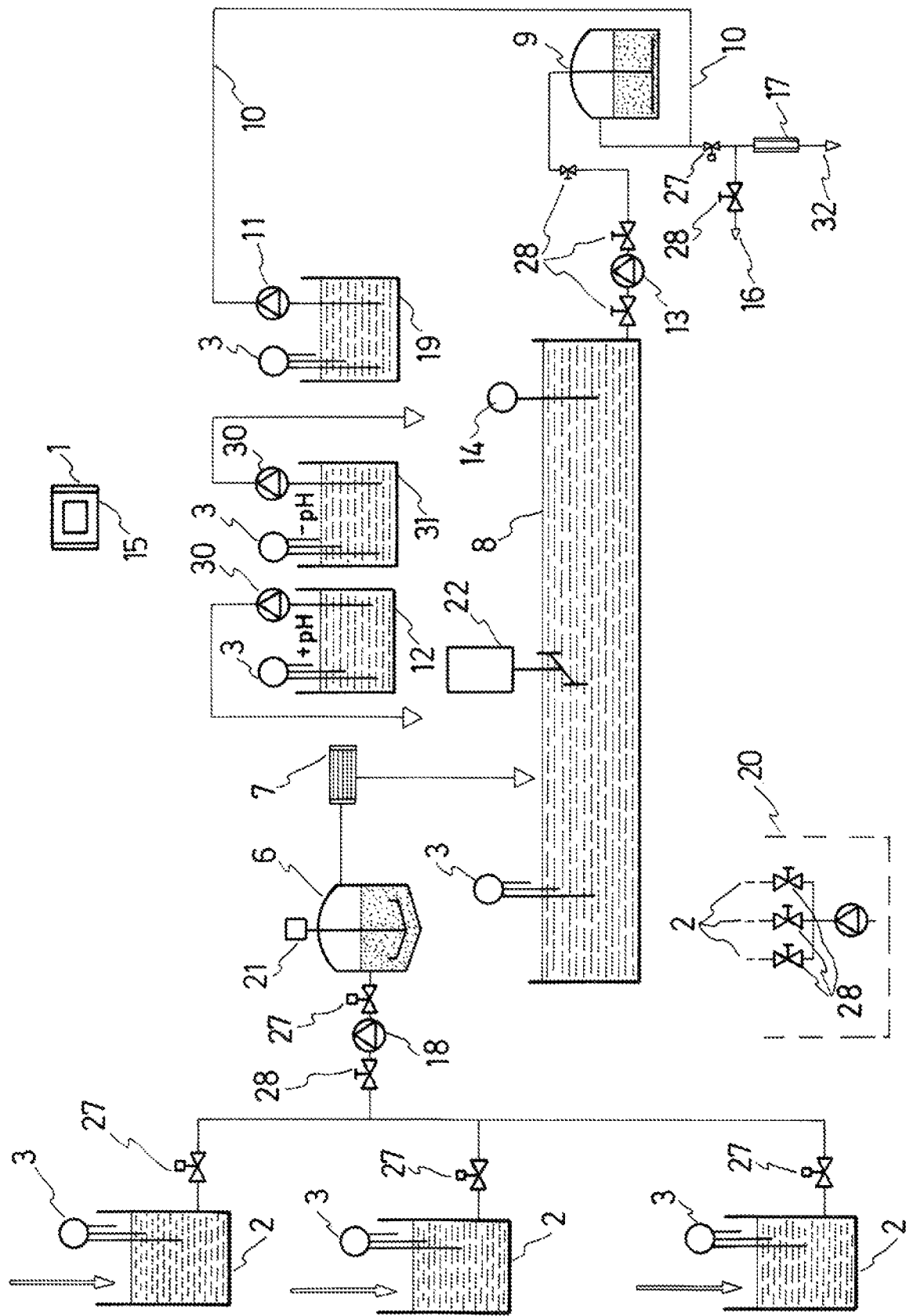

METHOD FOR TREATING DANGEROUS LIQUIDS FOR DUMPING

OBJECT OF THE INVENTION

The invention, as expressed in the title of the present specification, relates to a method for treating dangerous liquids for dumping.

More specifically, the object of the invention focuses on a method for treating the dangerous liquid waste of hospitals, clinics or industries, which is carried out in situ for dumping in the sewer once treated in a treatment plant using the necessary equipment for carrying out said method for treating dangerous liquid waste which is installed in the building.

FIELD OF APPLICATION OF THE INVENTION

The field of application of the present invention belongs to the sector of the industry dedicated to the treatment of dangerous aqueous liquid waste from hospitals and clinics or industries. Specifically, waste from processes involving chemical or biological materials with or without solids which can be highly harmful both to human health and the environment. Liquids with a high chloride, metal and BOD (Biochemical Oxygen Demand) and COD (Chemical Oxygen Demand) content.

BACKGROUND OF THE INVENTION

It is known that the removal of dangerous aqueous liquids from hospitals and clinics is carried out by waste management companies, with the risk of the hazardous nature of its road transport. It is removed without prior treatment. Hospitals are obliged to have a special waste collection point where dangerous liquids are deposited.

It is also known that hospitals and clinics are storing these liquids, for a limited period of time, until removal thereof.

The websites listed below are examples of the foregoing:
SESCAM (Castilla-La Mancha Health Service)
http://www.chospab.es/enfermeria/Documentos/Protocolo_Residuos.pdf
(Chapter I.II; Chapter III.II 2; Chapter III.II 3)
National Environment Conference
http://www.conama9.conama.org/conama9/download/files/CTs/985770_SGusi.pdf
Pages 5, 6, 7, 11, 19, 22, 23, 24, 25
HOSPITAL WASTE MANAGEMENT
Dr. Eng. Julián Uriarte Jaureguízar
http://www.osakidetza.euskadi.net/r85-pkpubl03/es/contenidos/informacion/comunicaciones_ambiental/eu_com/adjuntos/materialD esechable.pdf
Page 19

There is currently no such method of this type for treating dangerous liquids in situ at Hospitals and Clinics. At present, until removal thereof, the products are accumulated at a special waste collection site. The waste is subject to various handling operations, with the risk of contamination and personal injury. The liquids are removed by waste management companies, which involves further handling of drums and containers, pumping, road transport and discharge thereof, with additional risk of environmental pollution and personal injury.

EXPLANATION OF THE INVENTION

The method for treating dangerous liquids proposed by the invention applies, for example, to aqueous products from clinical analysis laboratories in hospitals and clinics or from processes involving chemical or biological materials with or without solids in industries is carried out immediately, continuously, 24 hours a day all year round, in situ.

Thus, prior to treatment, liquids arrive directly, preferably by means of piping without any prior handling, to different accumulation tanks provided in the plant, which is installed in situ, i.e. in the building that generates said liquids.

If the structure of the building impedes piping, the liquids can be discharged, without direct contact, into the different accumulation tanks in the treatment plant.

After treatment, the waste obtained is dumped into the sewer, always in compliance with the Municipal Ordinances in force.

Specifically, the treatment method comprises the following:

Dangerous liquids are accumulated in different accumulation tanks, depending on their origin and composition, and may be mixed or separated by their hazard level and non-compatibility with others. In the absence of piping, the plant will have a discharge station for drums, containers or any receptacle, for emptying into the accumulation tanks.

When one of the accumulation tanks reaches a sufficient accumulation volume for treatment, an evaporator is automatically filled, by pumping or by spilling thereof. Once the liquid reaches a specific level in the evaporator, the first phase of the treatment strictly speaking is initiated.

The evaporator is equipped with a heating system with a heat pump and operates, preferably, at a pressure below atmospheric pressure of 5 kPa and a temperature approximately between 30° C. and 34° C., although it can also range from 10° C. to 100° C.

Temperature exchange occurs in a conical or flat-type heating jacket. The heating and cooling means and systems installed in the user's building can also be used.

The interior of the evaporator jacket is continuously cleaned by an internal scraper. This design allows a high concentrate and distillate with very low conductivity. It is also possible to perform the process without using a scraper. The liquid can be heated directly or indirectly. Processing capacity is variable in terms of the amount of liters per day.

The aqueous parts are separated from the pollutant substances, which can be dissolved or in suspension, by means of the evaporation-concentration technique. This makes it possible to obtain a fully purified distillate and a concentrate that significantly reduces waste management costs.

Another advantage of the scraper is the obstacle of the formation of incrustations inside the heating jacket. The use or not of a scraper depends on the type of liquids to be treated.

After evaporation, the vapour is condensed in a condenser. The result is a purified distillate.

The condenser is continuously emptied into a neutralisation reactor. When it reaches a certain level, an agitator provided therein is started up.

Reagents are dosed to raise or lower pH in accordance with the pH permitted by the Municipal Ordinances in force for the dumping of waste into the public sewer. This process is continuous or discontinuous. Since the conductivity of the liquid after evaporation and condensing is very low, the cost of pH corrector is minimal.

The continuous or discontinuous process can be programmed. Evaporation is variable, depending on whether neutralisation is continuous or discontinuous.

In accordance with the types of liquids to be treated, a silicone or non-silicone antifoaming agent is also dosed during the process, at points defined depending on the liquids that can create foams.

After a certain waiting period, if changes in pH, conductivity or other parameters do not take place, a discharge pump is started up that carries the liquid to the sewer, once the waste has passed through an active carbon filter.

If not, an alarm is activated in the electrical panel provided in the plant, displaying the type of malfunction so a technician can act accordingly.

Adsorption by the active carbon filter is a step where a solid is used to eliminate soluble substances, such as the possible solvent content of the water, as a final safety treatment. Granular active carbon (GAC) is used in the filter. The activated carbon filter is necessary or not depending on the types of liquids to be treated.

In the event that the programmed ph and conductivity values are within the necessary minimum and maximum parameters, a disinfectant dosing pump is started up at the same time that the discharge pump that expels the liquids into the sewer is started up.

For safety reasons, the waste passes through an ultraviolet light with a wavelength of 254 to 270 nm.

The waste passes through said wave for the purpose of controlling and eliminating microorganisms by damaging their DNA (deoxyribonucleic acid). The damage caused by the ultraviolet light does not have known negative effects on water. The ultraviolet light penetrates the cell wall of a microorganism and causes a reaction in the microorganisms' DNA, breaking the C=C carbon link. This causes cell death, inhibiting the microorganism's capacity to grow and multiply.

Should the liquid disinfectant fail, either due to lack thereof, malfunction of the dosing pump or for other reasons, the ultraviolet light will act as an additional safety measure which is continuously available.

The plant has a sample-taking tap provided before the outlet of the sewer.

All the parameters, such as pH, conductivity, treatment cycles and anomalies, are saved in the memory of the automaton provided in the electrical panel, optionally envisaging the possibility of saving them in an external memory.

DESCRIPTION OF THE DRAWINGS

To complement to the description being made and for to aid towards a better understanding of the characteristics of the invention, the present specification is accompanied by a diagram constituting an integral part thereof which, by way of illustration and not limitation, represents the following:

FIG. 1. Shows, in a schematic flow diagram, a representation of the equipment that the plant comprises to carry out the method for treating dangerous liquids that is the object of the invention.

PREFERRED EMBODIMENT OF THE INVENTION

In light of FIG. 1 described above, a non-limiting example of the plant wherein the treatment method of the invention is carried out can be observed, whose main parts and elements have been designated with the following numerical references:

1 Electrical panel with automaton (processor) and remote control
2 Aqueous liquid accumulation tanks
3 Accumulation tank level probes
6 Evaporator
7 Condenser
8 Neutralisation reactor
9 Active carbon filter
10 Final disinfecting channelling pipe
11 Disinfectant dosing pump
12 pH+ reagent tank
13 Discharge pump
14 pH and conductivity probe
15 Cycle, pH, conductivity, anomalies/alarms log
16 Sample-taking tap
17 Ultraviolet light
18 Evaporator loading pump
19 Disinfectant tank
20 Drum discharge station
21 Scraper
22 Agitator
27 Automatic valves
28 Manual valves
30 Reagent dosing pump
31 pH− reagent tank
32 Drainage outlet of the sewer As can be observed in said FIG. 1, the treatment method is carried out in a plant installed in situ and comprises the following phases:

Collection of the dangerous liquids in one or more accumulation tanks (2), which have a volume between 100 and 5,000 liters, are made of materials resistant thereto, such as polypropylene, stainless steel, polyethylene or other materials, are rectangular, square or cylindrical, with or without a platform, underground or not and, in any case, preferably, are equipped with a permanent control by level probes (3). Said collection, preferably, is performed directly through a pipe but, in the absence thereof, is performed at a drum discharge station, for pumping, or other form of emptying, thereof into the accumulation tanks (2).

Evaporation, in an evaporator (6) which is automatically filled with the liquids of the accumulation tanks (2) when any of said tanks reaches the envisaged level, by means of a loading pump (18) and which, preferably, has a scraper (21) which, in a preferred embodiment, is started up at the same time as said pump. Although evaporation is continuous, the accumulation tanks (2) can continue to store dangerous liquids. The transfer of the liquid from the accumulation tanks (2) to the evaporator (6) is performed by means of automatic (27) and/or manual (28) valves and the filling of the evaporator (6) is controlled by an internal level probe (not shown).

In order to achieve evaporation, the evaporator (6), preferably, is equipped with a heating system with a heat pump and operates, preferably, at a pressure below atmospheric pressure of 5 kPa and at a temperature approximately between 30° C. and 34° C.

Should there not be sufficient dangerous liquids in the accumulation tanks (2), the process switches to "Standby" mode. As soon as there are sufficient dangerous liquids in the accumulation tanks (2), the process continues automatically.

Condensing in a condenser (7), which is online, in direct or indirect contact, with the vapour of the evaporator (6) and is actuated by the same, converting said vapour into a distillate. For said condensing, the condenser (7) uses the temperature of a cold/heat pump (not shown) or any external source or combination thereof.

Neutralisation of the distillates obtained using reagents, which is carried out in a neutralisation reactor (8) consisting of a rectangular, square or cylindrical recipient made of polypropylene, stainless steel or polyethylene material with a volume between 100 and 4,500 liters, the filling of which is controlled by another level probe (3) in continuous mode with the distillate flowing out of the condenser (7). When it reaches a certain level, controlled by the aforementioned level probe (3), an agitator (22) provided therein is started up.

Neutralisation in the neutralisation reactor (8) of the distillate is carried out at a pH controlled by a pH and conductivity probe (14), with reagents of corresponding tanks provided for such purpose, one pH+ (alkaline) reagent container (12) and another pH– (acid) reagent container (31) to raise or lower it, and whose dumping is performed using corresponding dosing pumps (30), always in compliance with the applicable Municipal Ordinances regulating dumping in the sewer. The tanks containing reagent (12 and 31) are controlled by level probes (3).

Filtering and disinfecting. When the product's pH and conductivity values, programmed in the automaton of the control panel (1) and controlled through the aforementioned pH and conductivity probe (14), are within the necessary minimum and maximum parameters, a disinfectant dosing pump (11), incorporated in a disinfectant tank (19), is started up simultaneously with a discharge pump (13) which expels the waste into the sewer and doses disinfectant therein, through the corresponding pipe (10), after previously passing the waste through an active carbon filter (9) provided behind said discharge pump (13). The disinfectant tank (19) is also controlled by a level probe (3). Furthermore, the discharge pump (13) empties the neutralisation reactor (8) in its entirety, controlled by another level probe (3) provided therein, whereupon the treatment method starts again.

It should be noted that disinfecting is performed using any reagent or liquid and/or gaseous liquid product, and liquid or solid colouring agents may also be incorporated in the treatment.

Safety disinfecting. Preferably, for safety reasons, the waste passes through an ultraviolet light (17) at between 253.7 and 270 nm wavelength provided before the drainage outlet of the sewer (32).

Sample-taking. Optionally, sample-taking of the waste is envisaged by means of a sample-taking tap (16) provided before the outlet of the sewer.

This sample-taking tap (16) and the pipes from the neutralisation reactor (8) and the active carbon filter (9) at the outlet of the sewer (32) include corresponding automatic (27) and manual valves (28).

Furthermore, all the parameters, such as pH, conductivity, treatment cycles and anomalies/alarms are recorded in a log (15) in the memory of the automaton processor provided in the electrical panel (1) that controls the whole system, envisaging the possibility of an external memory. Anomaly alerts will be made through any means.

Lastly, the process envisages the automatic or manual control of concentrated sludge and the manual or automatic evacuation thereof.

Having sufficiently described the nature of the present invention, in addition to the manner in which to put it into practice, it is not considered necessary to further extend its explanation so that any person skilled in the art can understand its scope and the advantages arising therefrom, stating that, within its essentiality, it can be put into practice in other forms of embodiment that differ in detail from that indicated by way of example and that will also fall under the protection sought, provided that its essential principle is not altered, changed or modified.

The invention claimed is:

1. METHOD FOR TREATING DANGEROUS LIQUIDS FOR DUMPING, characterised in that it is carrried out in a plant whose equipment is connected to an electrical panel (1) having an automaton processor which is installed in situ, comprising the following essential phases:
    collection of dangerous liquids, mixed or separated, in accumulation tanks (2), with a volume between 100 and 5,000 liters, made of materials resistant thereto, such as polypropylene, stainless steel, polyethylene or others, rectangular or cylindrical, with or without a platform, underground or not;
    evaporation, in an evaporator (6) which is filled automatically by a loading pump (18) or other means, with the liquids of the accumulation tanks (2), producing evaporation with an internal or external heating system;
    condensing in a condenser (7) which is online, in direct or indirect contact, with the vapour of the evaporator (6) and is actuated with the same, converting said vapour into a distillate;
    neutralisation of the distillates obtained by means of reagents, in a neutralisation reactor (8) consisting of a rectangular, square or cylindrical receptacle made of polypropylene, stainless steel or polyethylene material with a volume between 100 and 4,500 liters which is filled with the distillate flowing out of the condenser (7);
    filtering of the waste using an active carbon filter (9) and dosing of disinfectant therein, before being expelled through the drainage outlet of the sewer (32).

2. METHOD FOR TREATING DANGEROUS LIQUIDS FOR DUMPING, according to claim 1, characterised in that it also comprises a safety disinfecting phase using ultraviolet light (17).

3. METHOD FOR TREATING DANGEROUS LIQUIDS FOR DUMPING, according to claim 1, characterised in that it also comprises a sample-taking phase through a sample-taking tap (16) provided before the drainage outlet to the sewer (32).

4. METHOD FOR TREATING DANGEROUS LIQUIDS FOR DUMPING, according to claim 1, characterised in that the collection of dangerous liquids in accumulation tanks (2) is carried out directly through a pipe.

5. METHOD FOR TREATING DANGEROUS LIQUIDS FOR DUMPING, according to claim 1, characterised in that the collection of dangerous liquids in accumulation tanks (2) is carried out at a drum discharge station (20) for pumping, or other form of emptying, thereof into the accumulation tanks (2).

6. METHOD FOR TREATING DANGEROUS LIQUIDS FOR DUMPING, according to claim 1, characterised in that the neutralisation of the distillate in the neutralisation reactor (8) is carried out at a pH controlled by a pH and conductivity probe (14), using reagents from corresponding tanks provided for such purpose, a pH+(alkaline) reagent container (12) and another pH- (acid) reagent container (31) to raise or lower it.

7. METHOD FOR TREATING DANGEROUS LIQUIDS FOR DUMPING, according to claim 1, characterised in that all the parameters, such as pH, conductivity, treatment cycles and anomalies/alarms are recorded in a log (15) in the memory of the automation processor provided in the electrical panel (1) that controls the whole system.

* * * * *